US 7,419,102 B2

(12) United States Patent
Harris, Jr.

(10) Patent No.: US 7,419,102 B2
(45) Date of Patent: Sep. 2, 2008

(54) DISPENSER FOR SCENTS AND AROMAS

(76) Inventor: Rano J. Harris, Jr., P.O. Box 7259, Spanish Fort, AL (US) 36577

( * ) Notice: Subject to any disclaimer, the term of this patent is extended or adjusted under 35 U.S.C. 154(b) by 95 days.

(21) Appl. No.: 11/243,408

(22) Filed: Oct. 4, 2005

(65) Prior Publication Data

US 2006/0071092 A1    Apr. 6, 2006

Related U.S. Application Data

(60) Provisional application No. 60/616,014, filed on Oct. 5, 2004.

(51) Int. Cl.
*A61L 9/04* (2006.01)
(52) U.S. Cl. .............. 239/48; 239/6; 239/44; 239/47; 239/52; 239/145
(58) Field of Classification Search .......... 239/44, 239/47, 48, 52, 50, 55, 46, 49, 51, 51.5, 57, 239/145, 326; 43/1; 222/187
See application file for complete search history.

(56) References Cited

U.S. PATENT DOCUMENTS

| | | | |
|---|---|---|---|
| 4,302,899 A | 12/1981 | DeHart | |
| 4,374,571 A | 2/1983 | Hirvela | |
| 4,523,717 A * | 6/1985 | Schwab | 239/56 |
| 4,788,787 A | 12/1988 | Koniezki | |
| 5,074,439 A | 12/1991 | Wilcox | |
| 5,307,584 A | 5/1994 | Jarvis | |
| 5,832,648 A | 11/1998 | Malone | |
| 5,857,281 A | 1/1999 | Bergquist | |
| 5,947,379 A * | 9/1999 | Freeman | 239/52 |
| 6,085,989 A | 7/2000 | Cox | |
| 6,102,301 A | 8/2000 | Tiedemann | |
| 6,158,668 A | 12/2000 | Burgeson | |
| 6,241,161 B1 * | 6/2001 | Corbett | 239/58 |
| 6,820,363 B1 * | 11/2004 | Averette, Jr. | 43/1 |

OTHER PUBLICATIONS

Frados, Joel, Plastics Engineering Handbook, 1976, Van Nostrand Reinhold Company, fourth edition, pp. 71-73.*

* cited by examiner

*Primary Examiner*—Len Tran
*Assistant Examiner*—Jason J Boeckmann
(74) *Attorney, Agent, or Firm*—David E. Mixon; Bradley Arant Rose & White LLP

(57) ABSTRACT

A dispenser for scents and aromas is disclosed. The scent dispenser includes a hollow central body that contains a rotating shaft. A wick is wound around the shaft and extends through an opening in the top of the central body. A sealable cap is included to allow scent material to be added to the wick inside the central body. Finally, a suspension mechanism in included to allow the dispense to be suspended from a separate structure.

19 Claims, 11 Drawing Sheets

DISPENSER FOR SCENTS AND AROMAS

CROSS-REFERENCE TO RELATED APPLICATIONS

This application claims priority from U.S. Provisional Patent Application No. 60/616,014 entitled "Dispenser for Scents or Aromas" that was filed on Oct. 5, 2004.

BACKGROUND OF INVENTION

1. Field of the Invention

The invention relates generally to hunting equipment. More specifically, the present invention relates to a dispenser for scents and aromas.

2. Background Art

The use of scented formulations to attract game or fur bearing animals by hunters and trappers is a time-honored technique that has been in use for at least 100 years. A variety of natural and synthetic formulations are utilized to appeal in a variety of ways to the olfactory senses of the animals, whether to arouse the animals' curiosity or to otherwise attract such animals to the location of the hunter's blind or the trapper's trap. Quite often, such materials, usually in liquid form, have been derived from the urine or glandular secretions of such animals, and are, in many cases, quite odorous and foul-smelling. Other types of scents designed to mask or conceal the odor or scent trail of a hunter or trapper are also in common, widespread use, including such fragrances as cedar, pine, and fresh earth.

In the mid-to-late twentieth century, the use of deer urine-based scents, in particular, became popularized by individuals and companies who began bottling and selling such animal fluids as an effective way to attract game animals, in particular, whitetail deer. Such scents were most commonly used by pouring them onto the ground in the area where the hunter had chosen to hunt, which technique commonly resulted in spills and leakage of the foul-smelling scents onto the hands and clothes of the user. Likewise, in pouring the scents onto the ground, much of the scent ended up being absorbed into the ground, which resulted in inefficient evaporation and dispersal, and excessive expense inasmuch as once the expensive scent was poured out, it could not be re-used.

Devices for storage and dispersal or propagation of scented materials are widely known in the art. A variety of containers housing and selectively exposing an absorbent material upon which a scented material is placed, to permit passive evaporation of such scents, is known. Such devices generally do not satisfy the need for a clean, convenient, compact, and leak-free way to handle, store, and disperse scents, and in the vast majority of cases, they do not provide optimum scent dispersal due to the limited surface area of the scent-absorbent material or scent-containing medium, some of which constitute no more than a small piece of cotton, felt or sponge material. Likewise, many of the scent containers and scent dispersal devices known in the art do not provide for adequate sealing of the containers, resulting in frequent leaks and spills of very malodorous materials. Furthermore, such devices often tend to be large and bulky, and frequently involve complicated, often failure-prone mechanisms. Finally, in most cases no adequate provision is made for loading the scent, deploying the device, and storing the scent without the user ever having to touch or come into contact with the often foul-smelling scented materials. The present invention is directed at providing just such an improved device and method for storing and efficiently dispersing hunting, trapping, and other scented materials.

SUMMARY OF INVENTION

In some aspects, the invention relates to a scent dispenser, comprising: a hollow central body with a first opening on a first end and a second opening on the top; a rotatable shaft located within the central body; a wick that is wound around the rotatable shaft, where one end of the wick extends out of the central body through the second opening on top of the central body; a sealable cap that provides access the interior of the central body through the first opening so that scented material can be added to the wick; and a suspension mechanism on the exterior of the central body that allows the scent dispenser to be suspended from a separate structure.

In other aspects, the invention relates to ascent dispenser, comprising: a hollow central body with a first opening on a first end and a second opening on the top; means for storing a wick in the interior of the central body so that the wick maybe deployed at adjustable lengths through the second opening on the top of the central body; means for adding scented material to the wick in the interior of the central body that prevents spillage of the scented material; and means for suspending the scent dispenser from a separate structure.

A primary object of the present invention is to provide a simple, lightweight, and economical apparatus and method for the leak-free containment and efficient dispersal of scents used by hunters, gardeners, and others, in a design that is compact enough to permit easy carrying in a pocket or hunter's pack.

A further object and advantage of the device is to provide a container and dispenser for scented materials that is equipped with reliable seals at key locations to prevent the accidental leakage, spilling, or escape of the scented materials, which could otherwise contaminate the users clothing, gear, and hands.

A further object of the invention is to provide a simple, reliable, device which is very compact, yet provides a flexible, extendable, and elongated wick or other scent-containing medium which has a relatively very large surface area from which scent can evaporate and disperse, in order to maximize the amount of scent which is released into an area.

A further object of the invention is to provide a simple and reliable mechanism for extending and retracting the elongated wick or scented medium, and the ability to store the wick or scented medium within a very compact space inside the container, without leakage.

A further object of the invention is to provide simple, compact, leak-free scent storage and dispensing device which is compact and affordable, so that multiple units may be deployed in an area to provide even broader coverage, or to permit the use of multiple varieties of scents at the same time.

Another object and advantage of the device is to provide for easy and quick deployment of the device in the field, as well as quick and easy location and retrieval of the device after use.

A further object of the invention is to provide simple, compact, leak-free scent storage and dispensing device which, by attaching to an overhanging branch or support structure, elevates the scent vapor plume above the ground, to maximize dispersal of the scent throughout the surrounding area.

A further object of the invention is to provide a simple, compact, leak-free scent storage and dispensing device for hunters and others, which will not consume an excessively large amount of scent, and which affords the capability of storing the scent between uses, and re-using it at a later time, thereby reducing the amount of money spent on replacing scents during a given hunting season.

Another object and advantage of the invention is to provide for easy disassembly for cleaning, as when the user may wish to change the scented material being used, and to provide for easy and quick replacement of the wick or absorbent material or scented medium, as when the user desires to use another type of scent.

Other aspects and advantages of the invention will be apparent from the following description and the appended claims.

BRIEF DESCRIPTION OF DRAWINGS

It should be noted that identical features in different drawings are shown with the same reference numeral.

DETAILED DESCRIPTION

The present invention is directed to a lightweight, compact scent dispenser capable of storing and efficiently dispersing a variety of scented materials. The dispenser is particularly well-suited for the storage and dispersal of game attractant scents, such as urine-based or glandular-secretion-based materials, or synthetic versions thereof, for use in attracting animals such as deer while hunting or trapping. It is likewise well suited for containing, storing, and dispersing cover scents for hunters, fragrances for home and garden use, and for use in repelling various types of animals, ranging from quadrupeds to insects, through the use of suitable formulation which are repellent to various animal species.

The device includes a compact, simple container for containing, extending, and retracting an absorbent wick-type member or other scent-impregnated or scent-containing medium, which wick or scent-containing medium is utilized to hold the scented material until it the wick or scent containing medium is extended and exposed to the atmosphere and ambient wind currents, where such scented materials are released into the atmosphere to disperse the scented material's vapors throughout an area surrounding the location where the device is deployed.

In one embodiment, the dispenser includes a compact hollow main body which serves as a container for the wick or scent-containing medium when retracted into such container, and a side opening into the internal cavity of such hollow body through which the scent-containing medium is extended or retracted. The wick or scent-containing medium is attached at one end to an internal transverse shaft, equipped with a seal or gasket at the opening where it enters the container, and having a knob or handle attached to one external end of such shaft where it can be rotated by hand to extend the wick to expose and release the scent, or to retract the wick or scent-containing medium through the side opening into the container by winding it around the shaft. A filler cap is sealably and removably mounted to the end of the cavity opposite the knob or handle. Removing the filler cap permits access to the inner chamber of the container, and allows a liquid scented material to be applied to the coiled wick stored within. A second, hanger-cap is sealably mounted to the side opening into such hollow body to provide leak-tight storage for the scent when the wick or scented medium is fully retracted into the body. The opposite end of the absorbent wick or other scent-containing medium is attached to the hanger-cap. In addition, a hanging mechanism such as a cord or strap or hook is provided and attached to the upper portion of the hanger-cap, in order to provide the easy capability of mounting the unit to a tree branch or other elevated structure.

Figure 1:
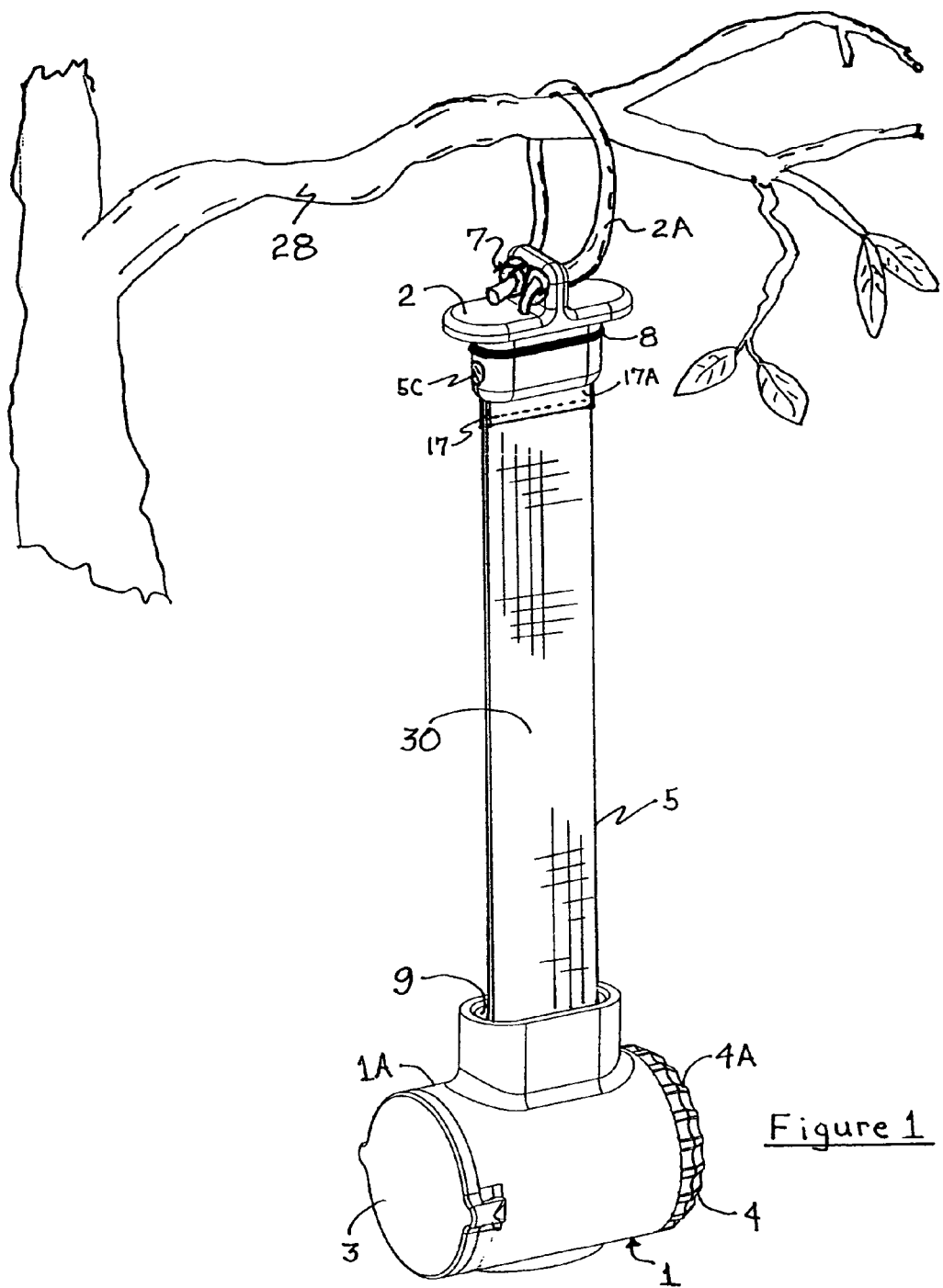
FIG. 1 is a view of a dispenser as deployed upon a branch, with the wick or scent-containing medium fully extended in accordance with one embodiment of the present invention.

Referring to FIG. 1, in one embodiment as shown, the container 1, including container body 1A, is fitted with a filler cap 3, a shaft-with-knob component 4, a flexible, extendable and retractable wick or other absorbent scent-containing or scent-impregnated medium 5. FIG. 1 further shows the device as it might be deployed for dispersal of scented materials in a hunting application, with the wick or scent-containing medium 5 fully extended to expose its full surface area 30 to the atmosphere and attached to an upper hanger-cap 2, which hanger-cap 2 is equipped with a cord, strap, or other apparatus 2A which is utilized for attachment of and suspension of the device from a tree branch or other elevated structure 28. By further referral to FIG. 1, it will be seen that the hook, cord, or strap 2A, which is attached to hanger cap 2 at one end, has been draped over such branch or elevated structure 28, and attached back to the hanger cap at notch 7.

Also as shown in FIG. 1, after the container 1 has been mounted upon a tree branch 28, the wick or scent-containing medium 5 has been extended by pulling the hanger cap 2 out of side opening 9 and apart from the main body 1A, thereby unwinding the wick or scent-containing medium 5 to its full length to expose its full surface area, and thereby permitting the release and evaporation of vapors of the scented materials from the generally flexible, elongate wick or scent-containing medium 5 to the ambient atmosphere, where the vapors of such scented materials can disperse on the wind currents to the surrounding area.

Figure 2:
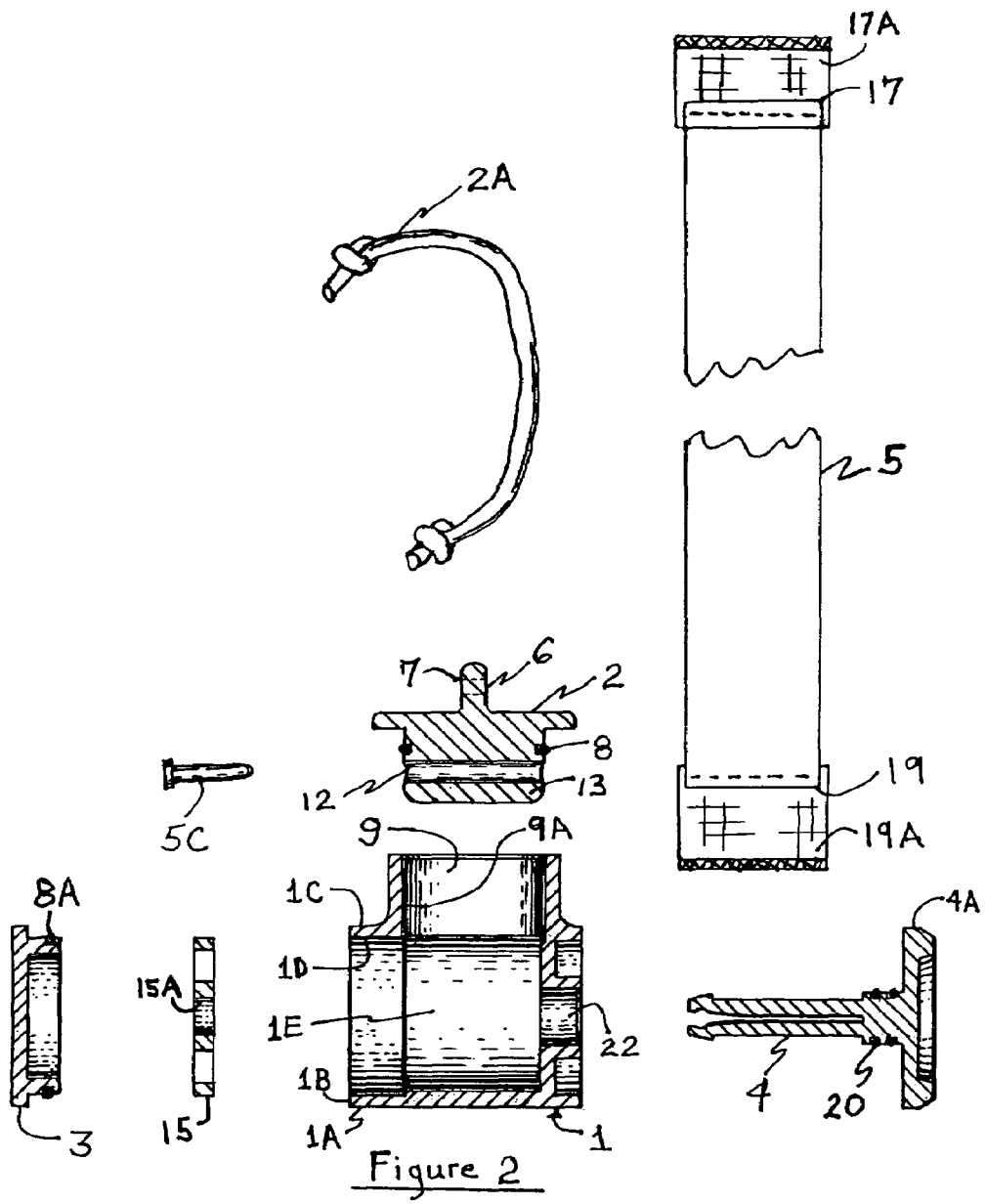
FIG. 2 is an exploded cross-sectional view of a dispenser, showing the main body comprising the container, a wick or scent-containing medium, a hanger cap, a knob for extending or retracting the wick or scent-containing medium, a filler cap, and structure on the hanger cap for the purpose of attaching a device such as a hook, string, or strap to suspend the container from an elevated structure such as an overhanging branch in accordance with one embodiment of the present invention.

Referring to FIG. 2, in one embodiment as shown, the container 1 is included of a main body 1A having a surrounding outer wall 1B that includes an outer wall surface 1C and an inner wall surface 1D, enclosing an inner chamber 1E. The container 1 is fitted with a hanger-cap 2, a filler cap 3, a shaft member 4 having a handle or knob section 4A, which may be integral to the shaft 4, or a separate piece which is attached thereto. The device is further equipped with a wick or scent-containing medium 5. In addition, the hanger cap 2 is equipped with a hole 6 and a hook-slot 7, for the purpose of attaching a hanger-cord 2A which is provided to suspend the container 1 from an elevated structure such as an overhanging branch or other elevated structure. The hanger cap 2 is equipped with a resilient O-ring 8, preferably made of an elastomeric or other suitably resilient polymeric material, suitably configured and sized to seal the circumference around hanger cap 2 when hanger cap 2 is inserted into the side opening 9, to prevent leakage or escape of scent vapors or liquid from the container 1 when the wick or scent-containing medium 5 is stored within the inner chamber 1E of main body 1A.

As shown in FIG. 2, in one embodiment of the invention, the cylindrical body 1A is equipped at one end with a cylindrical hole 22 that opens to the outside to the inner chamber 1E of the body 1A. A shaft member 4 is inserted into the hole 22. The end of shaft 4 which remains outside the inner chamber 1E of the body 1A, is configured with a handle or knob or similar device 4A to allow hand-rotation of the shaft 4 by the user, for the purpose of un-winding the wick or scent-containing medium 5 from the shaft 4 and to extend it to its full length, thereby exposing the scent to the atmosphere. After use, this embodiment enables winding the wick or scent-containing medium 5 around the shaft 4, thereby retracting the wick or scent-containing medium back into the inner cavity 1E of the main body 1A for storage.

In one embodiment, when the wick or scent-containing medium 5 is fully wound around the shaft and thus drawn into and contained within the inner chamber 1E, the hanger cap 2 is likewise drawn into the side opening 9, and the sealing O-ring or gasket 8 of the hanger cap 2 abuts the inner surface 9A of side opening 9, to prevent leakage of scent from the container 1. The top or outer end 17 of the wick or scent-containing medium 5 is fitted with a loop 17A which is utilized for attaching the wick or scent-containing medium 5 to hanger cap 2. Such loop 17A is positioned and retained within transverse hole 12 and transverse slot 13 of hanger-cap 2, by retainer-pin 5C mounted within loop 5A. The hanger cap 2 is likewise fitted with an O-ring or gasket 8 which forms a seal against the outer circumference of the hanger cap 2, and against the inner wall 9A of the side opening 9, when the hanger cap 2 is forced to the full depth into the side opening 9.

Figure 3:
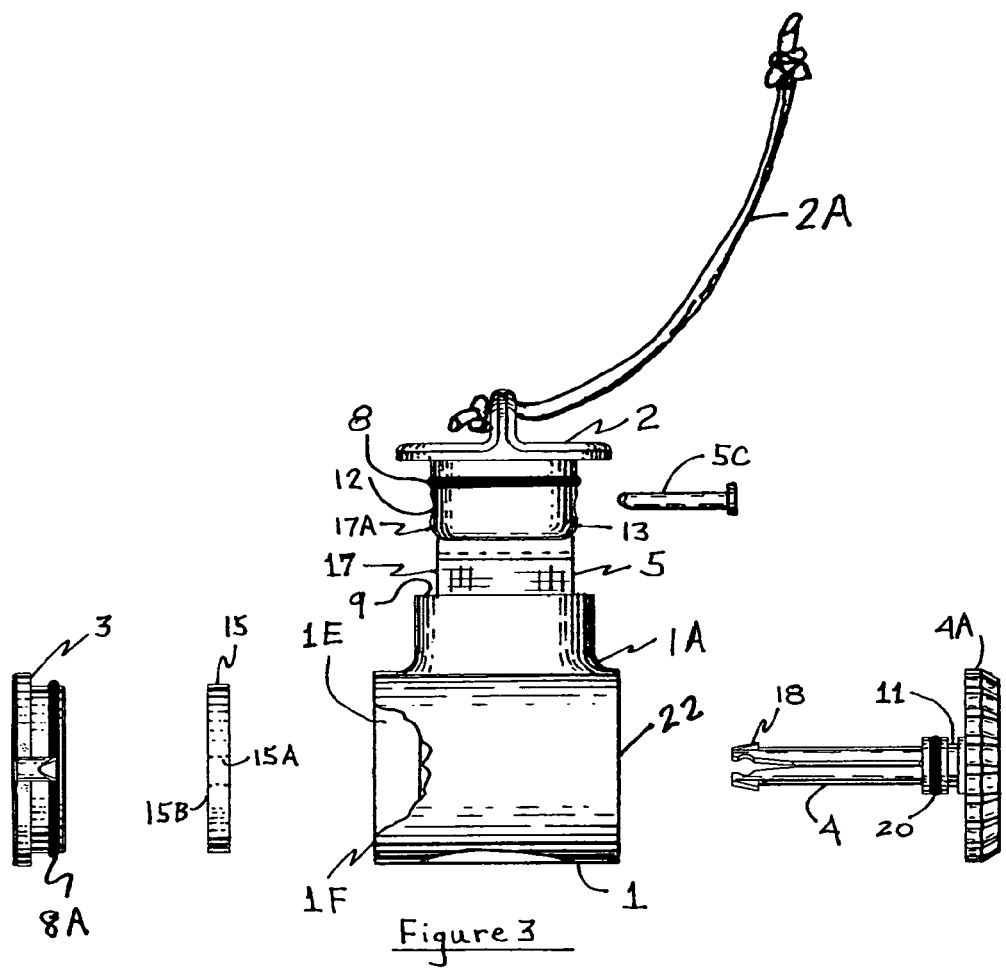
FIG. 3 is an exploded plan view showing the individual parts of a dispenser, including the main container body, the shaft, with knob, shaft-retaining ring, hanger cap, extendable wick or scent-containing medium, filler cap, wick or scent-containing medium retainer pin, hanger cord in accordance with one embodiment of the present invention.

FIG. 3 shows the inter-relationships of the various components of one embodiment of the invention. The main body 1A serves as the central mounting "chassis" for the container 1. The shaft 4 is sealably and rotatably mounted within the mating hole 22 in the end of main body 1A, with the seal being affected by one or more resilient O-rings or gaskets 20, installed in one or more grooves 11 in the circumference of shaft 4. The upper end 17 of the wick 5 is also equipped with a loop 17A, which slides through the transverse slot 13 in hanger cap 2, and transverse hole 12, and is held in place by retainer pin 5C which is placed within loop 17A while such loop 17A is contained within transverse hole 12 and transverse slot 13. The hanger cap 2 is likewise fitted with one or more resilient members, such as O-rings 8, to seal hanger cap 2 around its circumference against the inner wall surface of side opening 9, as the hanger cap 2 is inserted into the side opening 9.

Figure 4:
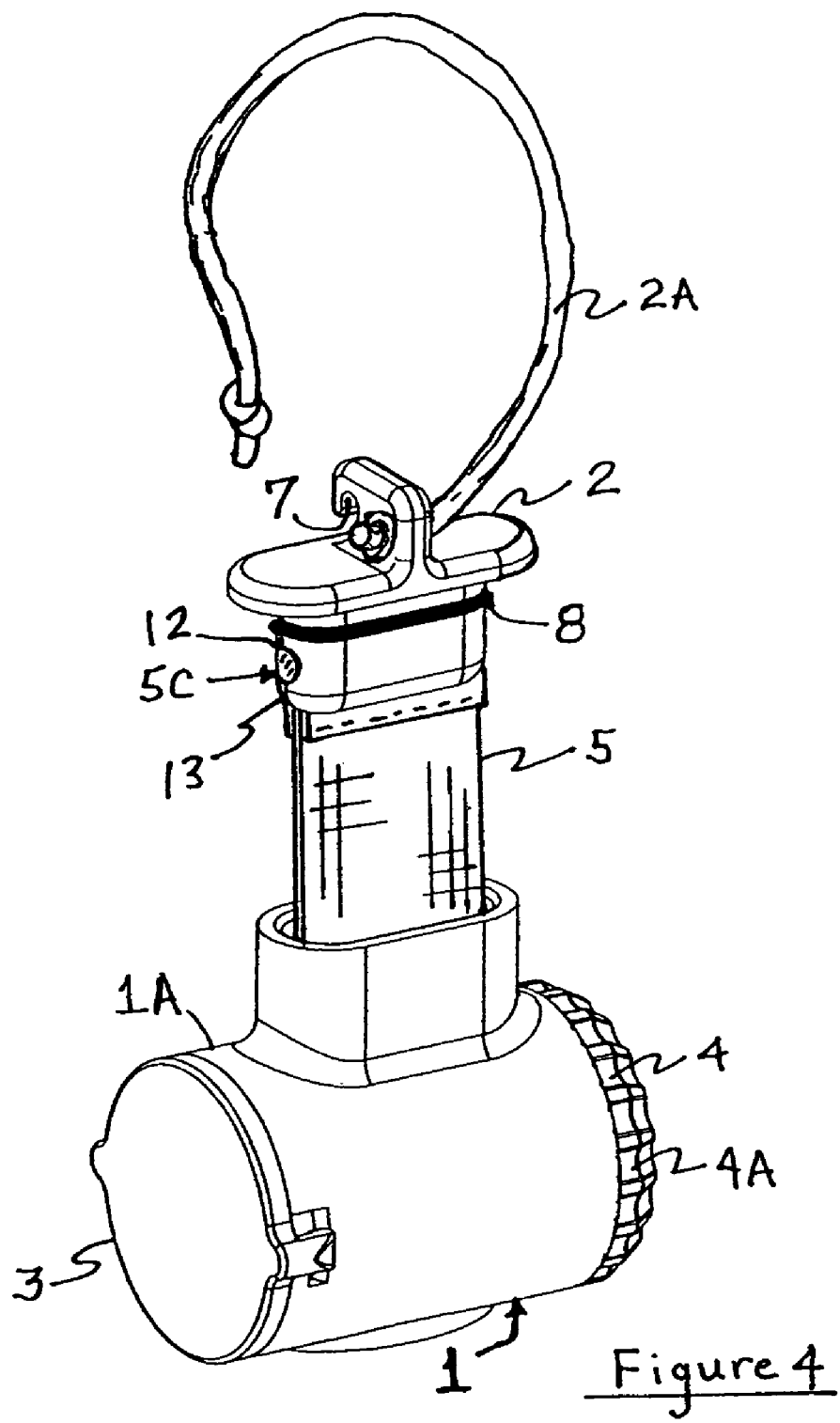
FIG. 4 is a perspective view of a dispenser, showing the filler cap, container body, shaft and knob, hanger cap, wick or scent-containing medium, retainer pin for the wick or scent-containing medium, O-ring seal for the hanger cap, and a hanger cord in accordance with one embodiment of the present invention.
Figure 5:
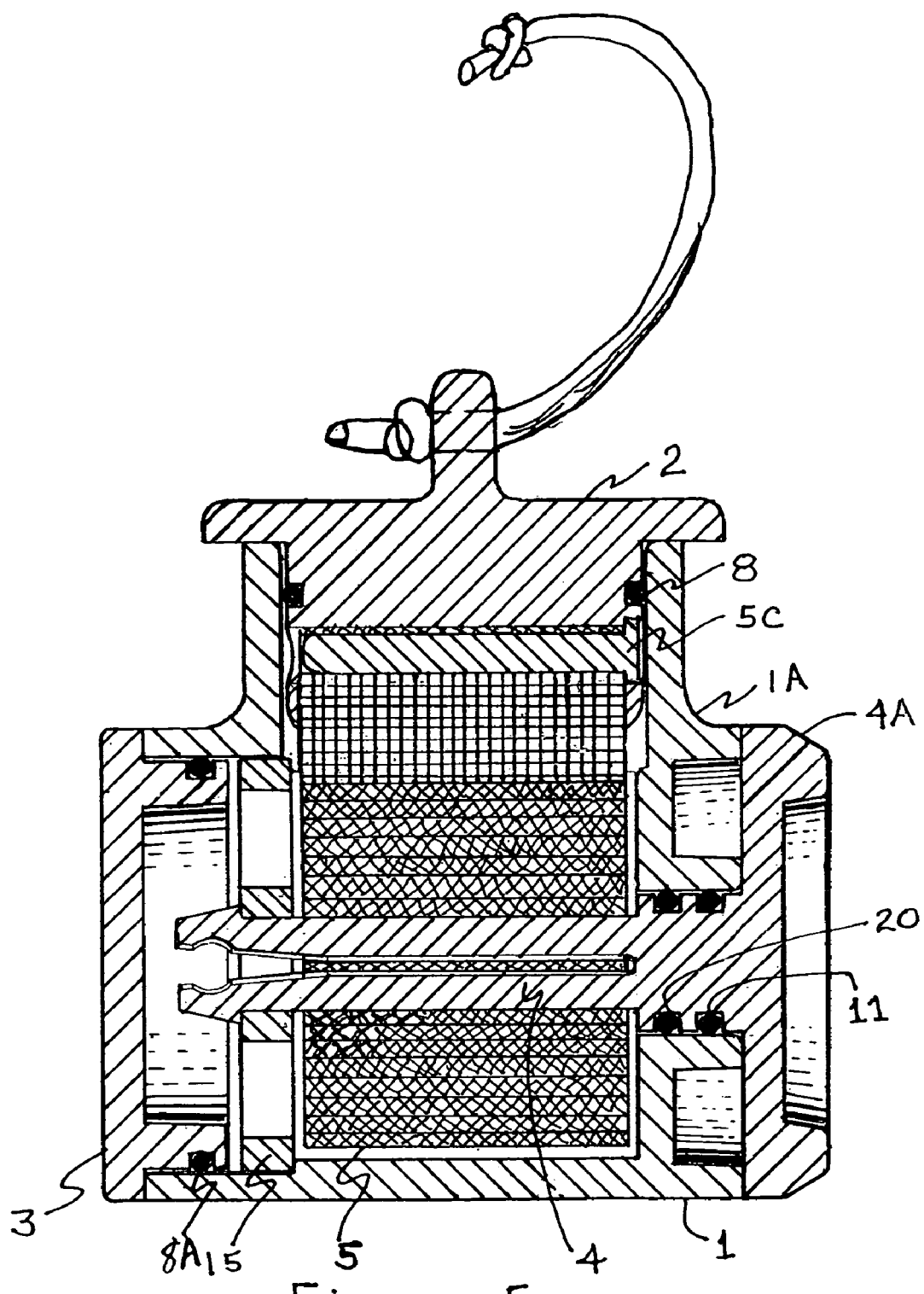
FIG. 5 is a cross-sectional view of a dispenser with all components assembled, showing the wick or scent-containing medium in its retracted position, wound around the shaft, with the hanger cap fully inserted to its full depth into the side opening of the body in accordance with one embodiment of the present invention.

In FIG. 4, the individual parts of one embodiment of the dispenser are shown, including the main container body 1A, the shaft 4 with knob 4A, hanger cap 2, extendable wick or scent-containing medium 5, filler cap 3, wick or scent-containing medium 5, retainer pin 5C, and hanger cord 2A. FIG. 5 illustrates the assembled relationships of the various components of one embodiment of the invention, including the filler cap 3, shaft retainer 15, container body 1A, shaft 4 and knob 4A, hanger cap 2, and retainer pin 5C for the wick or scent-containing medium 5, and hanger cord 2A, and O-rings 8, 20, and O-ring 8A on the filler cap 3.

Figure 6:
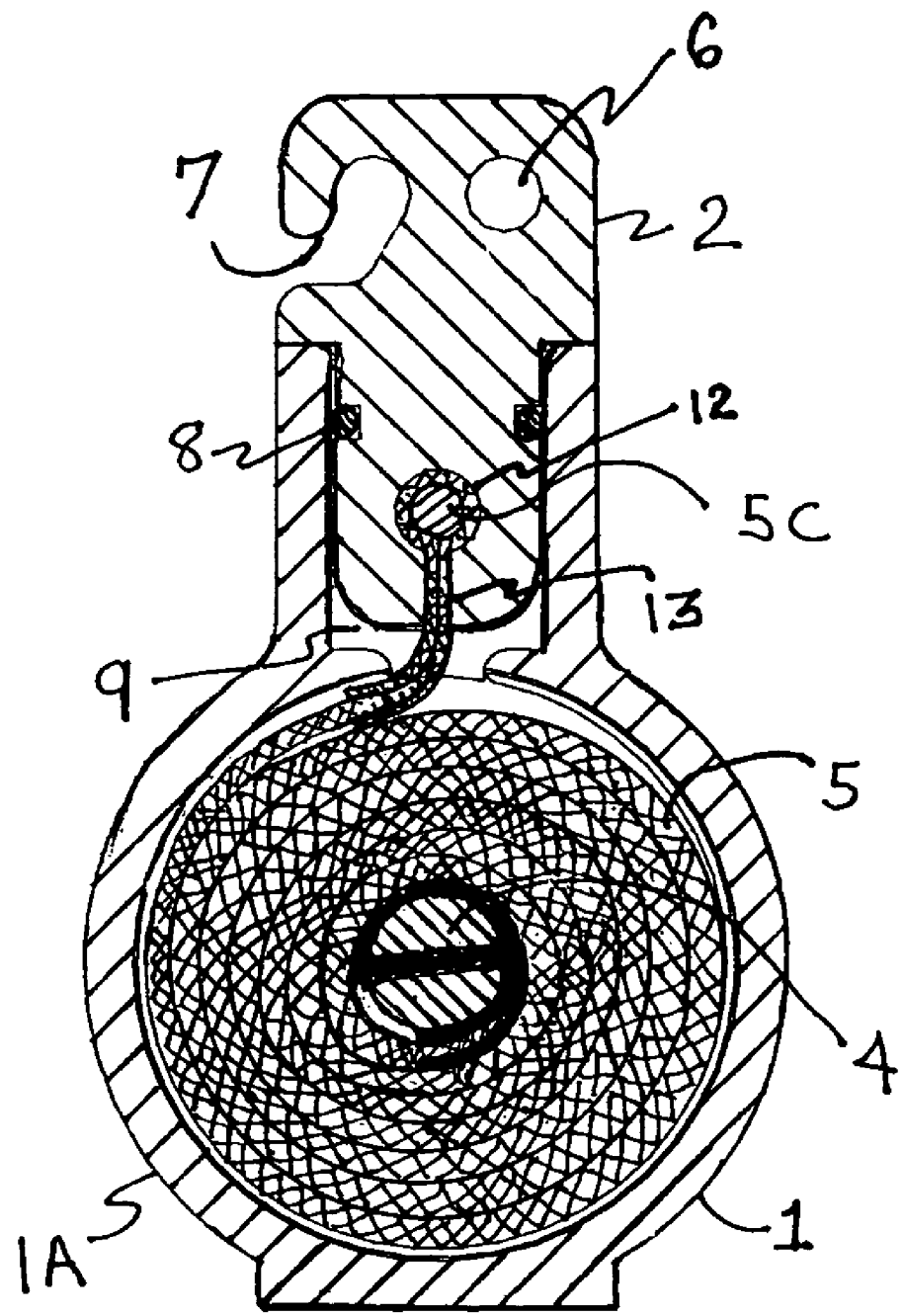
FIG. 6 is a cross sectional end-view of a dispenser with all components assembled, and revealing the placement and relationships of such components, including the wick or scent-containing medium wound around the shaft and fully retracted in accordance with one embodiment of the present invention.
Figure 7:
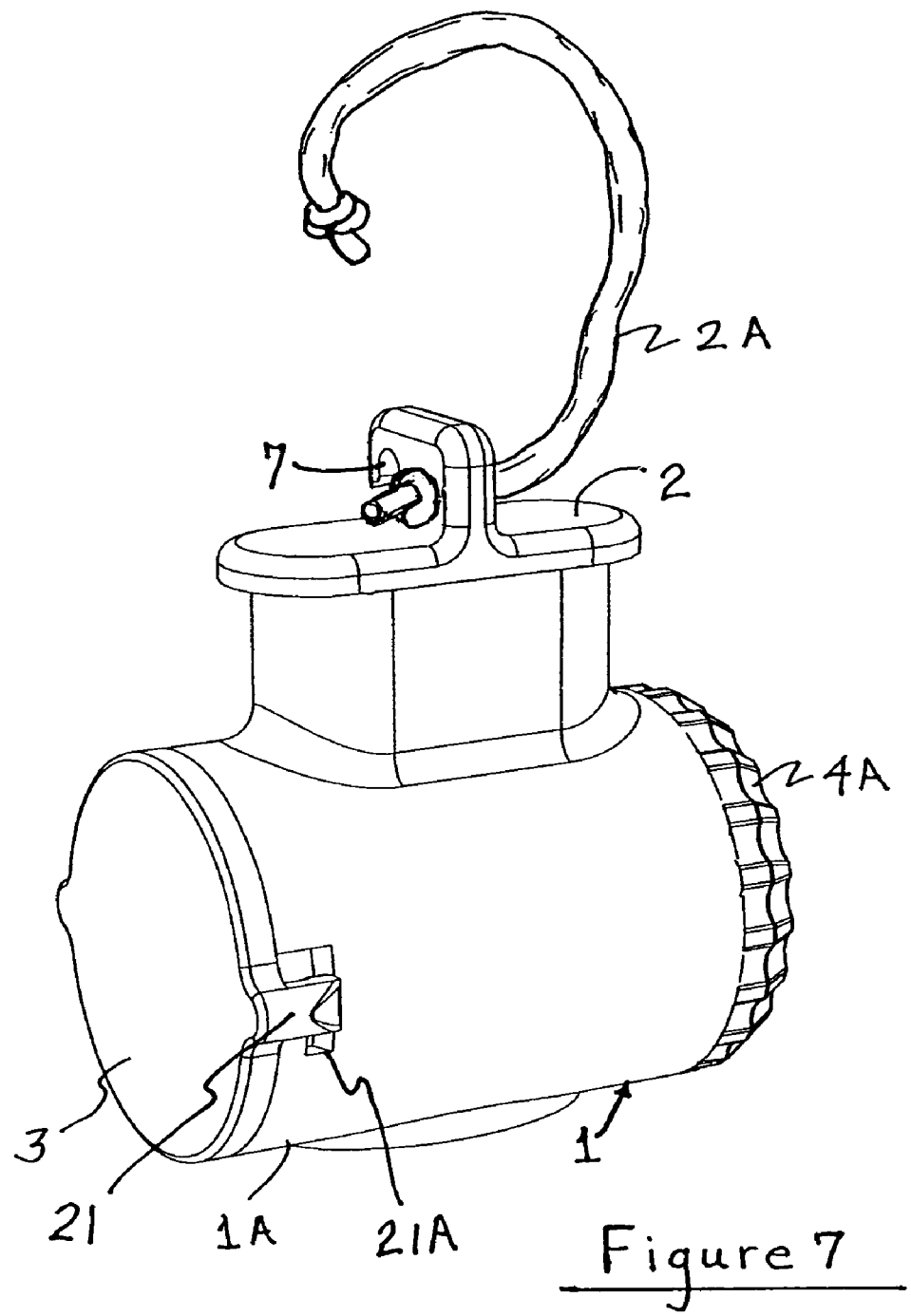
FIG. 7 is a perspective surface view of one embodiment of the fully-assembled scent containing and dispersal device, with both filler cap and hanger cap sealably attached to the main body, and revealing a cord or string utilized for attaching the device to a tree branch or other elevated structure.

In FIG. 6, a cross-sectional end-view of one embodiment of the device illustrates the container 1 and all components of the device assembled and contained in the main body 1A, showing the wick or scent-containing medium 5 in its retracted position, wound around the shaft 4, with the hanger cap 2 fully inserted to its full depth into the side opening 9 of the body 1A. FIG. 7 is a perspective exterior surface view of one embodiment of the fully-assembled scent containing and dispersal device, with both filler cap 3 and hanger cap 2 sealably and removably attached to the main body 1A, and revealing a cord or string 2A utilized for attaching the container 1 to a tree branch or other elevated structure 28 (not shown in this Figure).

Figure 8:
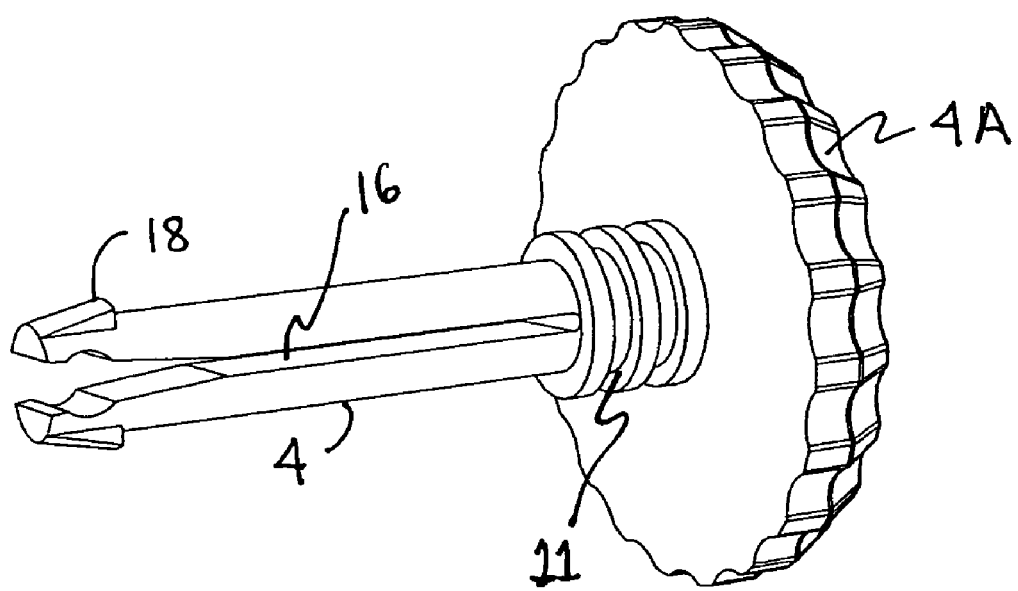
FIG. 8 is a perspective-drawing of the shaft of a dispenser, showing a pair of O-ring sealing grooves, a longitudinal slot configured to receive one end of a wick or other scent-containing medium, a knob for winding the wick or other scent-containing medium around the shaft, and a pair of nibs at the end at the end opposite the knob, which are provided for the purpose of retaining the shaft within the body by locking into the shaft retaining ring in accordance with one embodiment of the present invention.
Figure 9:
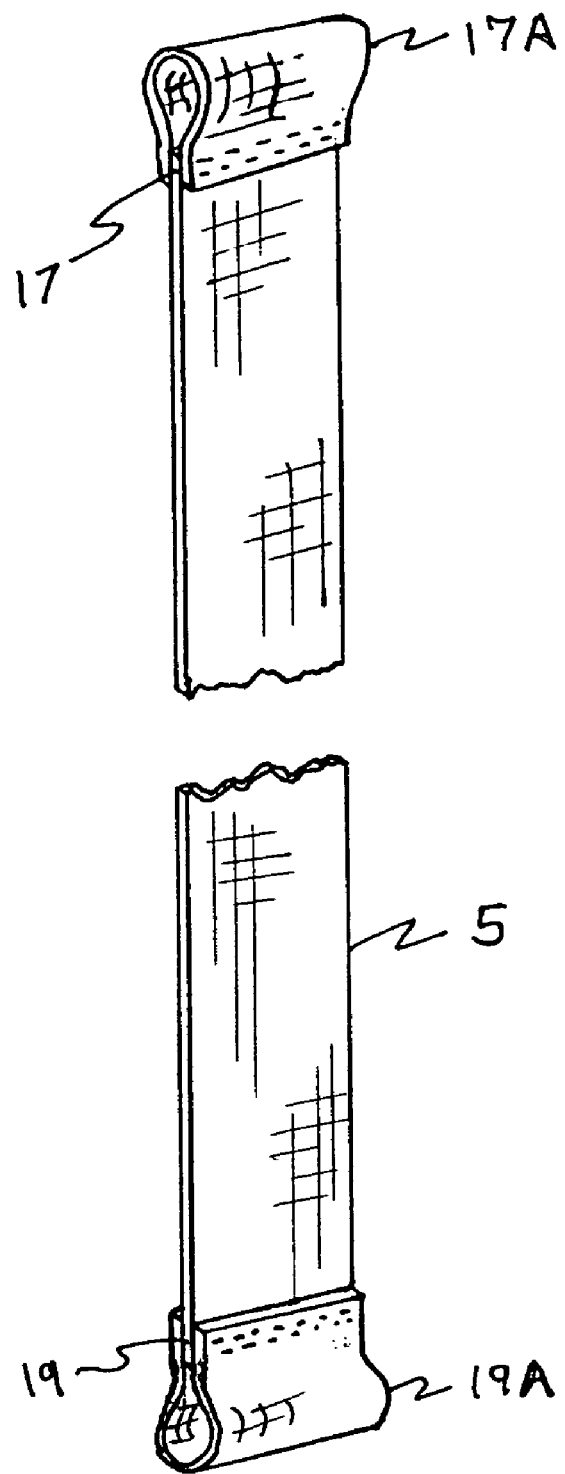
FIG. 9 is a perspective view of a wick or scent-containing medium, showing attachment loops affixed to or formed as a part of an upper end and a lower end of such wick or scent-containing medium in accordance with one embodiment of the present invention.

FIG. 8 illustrates the shaft 4 of one embodiment of the device, showing a pair of O-ring sealing grooves, a longitudinal slot configured within and parallel to the central axis of the shaft 4, and adapted to receive one end loop 19A of a wick or other scent-containing medium 5 as revealed in other figures, a knob 4A for winding the wick or other scent-containing medium 5 around the shaft 4, and a pair of nibs 18 at the end opposite the knob 4A, which are provided for the purpose of retaining the shaft 4 within the body 1A by locking into the shaft retaining ring 15 after being passed through opening 22, as in FIG. 5. FIG. 9 reveals one embodiment of a wick or scent-containing medium 5, with attachment loops 17A and 19A affixed to or formed as a part of an upper end and a lower end, respectively, of such wick or scent-containing medium 5.

Figure 10:
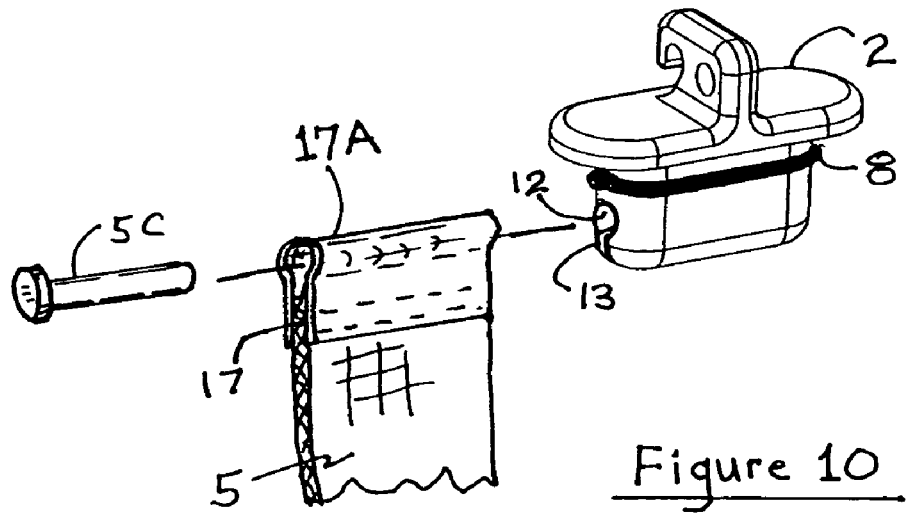
FIG. 10 is a perspective view of a dispenser that shows how a wick or other scent-containing medium may be attached to the hanger cap with a loop formed or attached at each end of such wick or scent-containing medium, and a retainer pin in accordance with one embodiment of the present invention.
Figure 11:
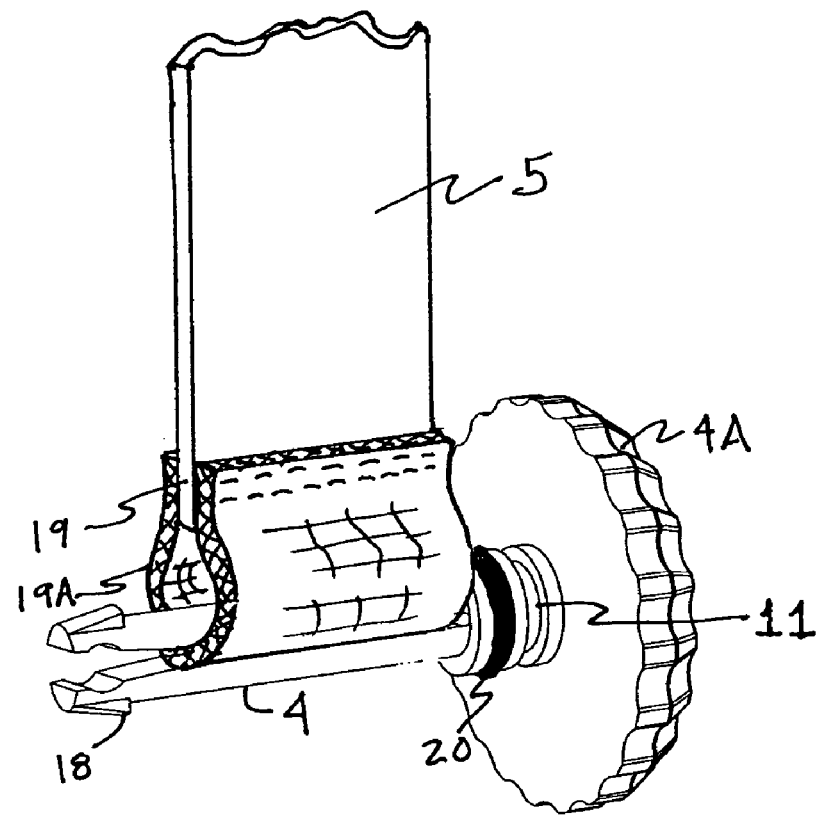
FIG. 11 is a perspective view of a dispenser that shows how a wick or other scent-containing medium may be attached to the shaft with a loop formed or attached at one end of such wick or scent-containing medium in accordance with one embodiment of the present invention.

FIG. 10 is a perspective view which shows how, in one embodiment of the device, a wick or other scent-containing medium 5 may be attached to the hanger cap 2, with a loop 17A formed or attached at the upper end 17 of such wick or scent-containing medium 5, and a retainer pin 5C, which are inserted into and retained within a transverse hole 12 and a transverse slot 13 by such retainer pin 5C. FIG. 11 is a perspective view which shows how a wick or other scent-containing medium 5 may be attached to the shaft 4, with a loop 19A formed or attached at the bottom or lower end 19 of such wick or scent-containing medium 5, which loop is inserted into and held within a center slot 16 of shaft 4.

Figure 12:
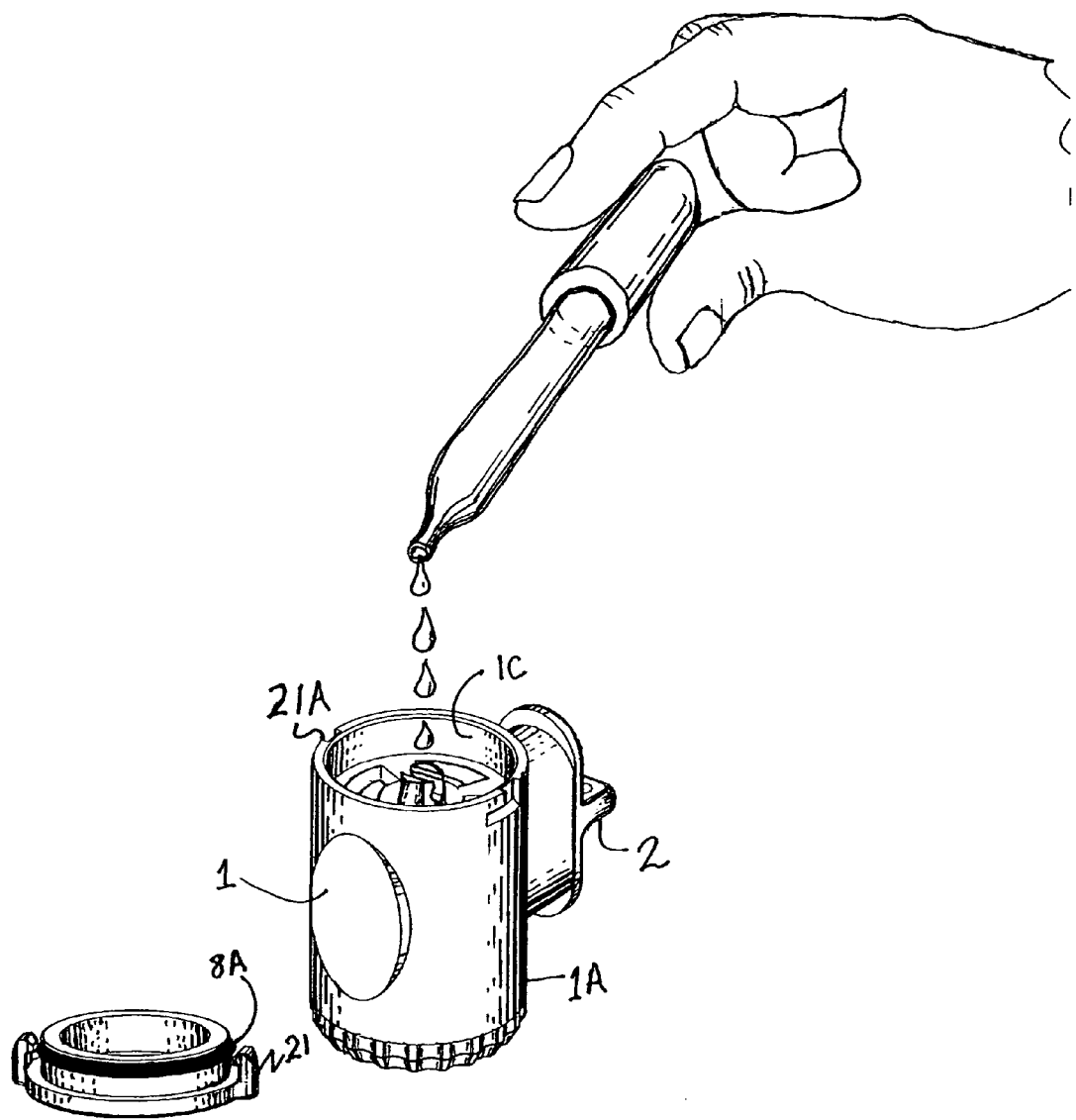
FIG. 12 is a perspective view of a dispenser with the filler cap removed, showing the stored wick or scent containing medium wound around the shaft within the inner chamber, and scent being added via an eye-dropper to saturate the wick or scent-containing medium in accordance with one embodiment of the present invention.

Referring to FIG. 12, removal of the filler cap 3 permits a quantity of scented material to be poured or otherwise loaded onto the absorbent wick or scent-containing medium 5, as shown, thereby loading such wick or medium 5 with scented material in preparation for future use. Alternatively, such wick or scent-containing medium 5 may be pre-soaked or pre-impregnated or infused with scented materials, as with a scent-containing medium made of a scent-impregnated plastic or other material, or a pre-loaded wick. When the filler cap 3 is fully inserted into the inner chamber 1E of main body 1A, the O-ring or gasket 8A seals against the inner wall surface 1C to prevent leakage or escape of the scent vapors or liquid. In one embodiment, a locking mechanism such as locking tabs 21 on filler cap 3 with mating locking grooves 21A may be utilized to retain the filler cap 3 in place, to prevent inadvertent removal of the cap 3, or to prevent any possible buildup of pressure within the container 1 from forcing the cap 3 out of the main body 1A. Upon replacement of the filler-cap 3, the scented material is retained on the scent-containing medium, and is sealed within the main cavity 1E of the main body 1A, until the user is ready to dispense the scent, possibly hours, days, or weeks later.

The container body 1A, shaft 4, hanger cap 2, filler cap 3, retainer pin 5A may all preferably be constructed of a suitable polymeric material, such as high-density polyethylene, polypropylene, ABS, or other thermoplastic, or other thermosetting or composite material such as glass-reinforced polyester resin. O-rings 4E, 8, and 19 are preferably constructed of a resilient elastomeric material such as nitrile rubber, viton, silicone, acrylonitrile or other such elastomer, or one of a number of fluorocarbon materials or elastomer/fluorcarbon composites. It will be obvious to those skilled in the art that the container 1 and its rigid solid components may be made in a number of different sizes, shapes, and colors, from a variety of materials, including the various types of polymers as listed above, and in addition the device may be equipped with a camouflage coating with several different processes, including film transfer and others.

Likewise, the elongate wick or scent containing medium 5, in a one configuration, may be made of a braided or woven cotton or other natural textile fabric that has been specially treated to remove natural oils and to render it hydroscopic and highly absorbent, and may be configured in various widths, thicknesses, lengths, and colors. Preferably, such wick or scent-containing medium 5 may be shaped as a flat, elongated strip of material having a thickness ranging from approximately 0.031" to about 0.25", but in one embodiment may be about 1/16" in thickness, with a length ranging from about 4" to as long as 3 or 4 feet or longer, but in one embodiment approximately 6" to 12" long. Such wick 5 is preferably configured as a flat solid woven or braided, or hollow woven or braided, textile fiber or fabric material having a width that may range from about 1/4" to as much as 4" wide, or more, but preferably, in an embodiment suitable for hunting, outdoor, household, or gardening use, having a nominal width of about 1/2" to 1". Alternatively, the wick or scent-containing medium 5 may be made from a range of materials such as natural or synthetic fabrics, plastics or polymers, scent-impregnated plastics or polymers, absorbent permeable, porous or foamed elastomers, foam plastics, felt materials made of natural or synthetic fibers, or other absorbent or adsorbent materials, and in a variety of shapes and sizes to accommodate a variety of applications and needs. Likewise, the dimensions and geometry of the main body 1D and associated components may be configured and constructed in a wide range of different sizes, colors, and shapes to accommodate scent-containing media or wicks of various types and sizes, without departing from the spirit and scope of this invention.

Numerous characteristics and advantages of the invention have been set forth in the foregoing description, together with details of the structures and function of the invention. The novel features of the invention are also pointed out in the appended claims. The disclosure, however, is illustrative only, and changes may be made in detail especially in matters of shape, size, materials, and arrangement of some of the parts, within the principle of the invention, to the full extent indicated by the broad general meaning of the terms express in the following claims.

What is claimed is:

1. A scent dispenser, comprising:

a horizontal hollow central body with a first opening on a first end of the body and a second opening on the top of the body where the second opening is formed by upwardly extended wails from the horizontal hollow central body to form a neck opening, where the first opening and second opening are sealed to form a reservoir for holding a liquid scented material without spillage;

a hanger cap with a transverse slot that extends laterally across the hanger cap, where the hanger cap seals the neck opening on top of the horizontal hollow central body;

a rotatable shaft located within the horizontal hollow central body, where the rotatable shaft has a longitudinal slot running along the length of the rotatable shaft and retaining nibs located on the distal end of the rotatable shaft;

a shaft retaining ring located in the interior of the horizontal hollow central body and having a circular opening in the center of the shaft retaining ring, where the nibs are inserted through the circular opening in and lock the rotatable shaft into place within the horizontal hollow central body while still allowing the shaft to rotate;

a rectangular wick with an attachment loop located on the upper and lower ends of the wick, where the attachment loop for the lower end of the wick is looped into the longitudinal slot of the rotatable shaft so that the wick is held on the rotatable shaft as the wick is wound and unwound around the rotatable shaft, and where the upper end of the wick extends out of the horizontal hollow central body through the neck opening on top of the central body and the attachment loop located on the upper end of the wick is inserted into the transverse slot in the hanger cap and held in place by a retainer pin that is inserted into the attachment loop on the upper end of the wick;

a filler cap that provides access the interior of the horizontal hollow central body through the first opening on the first end of the body so that any liquid scented material in the horizontal hollow central body is absorbed by the wick; and a suspension mechanism located on the hanger cap, where the suspension mechanism suspends the scent dispenser from a separate structure.

2. The scent dispenser of claim 1, where the wick comprises a natural fiber material.

3. The scent dispenser of claim 2, where the natural fiber material is cotton.

4. The scent dispenser of claim 3, where the cotton wick is woven.

5. The scent dispenser of claim 3, where the cotton wick is braided.

6. The scent dispenser of claim 2, where the wick has been chemically treated to remove oils, in order to render the wick highly absorbent and hydroscopic.

7. The scent dispenser of claim 1, where the wick comprises a synthetic fiber.

8. The scent dispenser of claim 7, where the synthetic fiber comprises dacron.

9. The scent dispenser of claim 7, where the synthetic fiber comprises polyester.

10. The scent dispenser of claim 7, where the synthetic fiber comprises polypropylene.

11. The scent dispenser of claim 7, where the synthetic fiber comprises nylon.

12. The scent dispenser of claim 1, where the wick comprises an elastomeric foam material.

13. The scent dispenser of claim 1, where the horizontal hollow central body is made of a thermosetting polymer.

14. The scent dispenser of claim 13, where the thermosetting polymer is polyester.

15. The scent dispenser of claim 13, where the thermosetting polymer is an epoxy resin.

16. The scent dispenser of claim 1, where the filler cap and the hanger cap are each sealed with an O-ring.

17. The scent dispenser of claim 1, further comprising:
a knob that is attached to the opposite end of the rotatable shaft from the nibs, where the knob extends through the horizontal hollow central body so that the rotation of the shaft may be controlled from the exterior of the horizontal hollow central body; and
an O-ring that seals the rotatable shaft as it extends through the central body.

18. The scent dispenser of claim 1, where the wick is pre-loaded with a scented material.

19. The scent dispenser of claim 1, where the wick is made of a scent-containing material.

* * * * *